United States Patent
Sabin et al.

(10) Patent No.: US 6,640,801 B2
(45) Date of Patent: Nov. 4, 2003

(54) HEAT PACK WITH EXPANSION CAPABILITY

(75) Inventors: Martin W. Sabin, Sarasota, FL (US); Cullen M. Sabin, Bradenton Beach, FL (US); Yan Xiong, Clearwater, FL (US); Kevin J. Pitz, Ruskin, FL (US)

(73) Assignee: Tempra Technology, Inc., Bradenton, FL (US)

( * ) Notice: Subject to any disclaimer, the term of this patent is extended or adjusted under 35 U.S.C. 154(b) by 0 days.

(21) Appl. No.: 09/942,851

(22) Filed: Aug. 29, 2001

(65) Prior Publication Data

US 2003/0041854 A1 Mar. 6, 2003

(51) Int. Cl.⁷ .................................................. A61F 7/00
(52) U.S. Cl. .................................. 126/263.01; 126/204
(58) Field of Search .......... 126/263.01, 263.05–263.09, 126/204; 206/222; 607/114

(56) References Cited

U.S. PATENT DOCUMENTS

| | | | |
|---|---|---|---|
| 3,906,926 A | * 9/1975 | Staples | 126/263.05 |
| 4,397,315 A | 8/1983 | Patel | |
| 4,773,389 A | * 9/1988 | Hamasaki | 126/263.07 |
| 4,793,323 A | * 12/1988 | Guida et al. | 126/263.08 |
| 4,895,135 A | * 1/1990 | Hamasaki | 126/263.07 |
| 4,974,419 A | 12/1990 | Sabin et al. | |
| 5,035,230 A | 7/1991 | Steidl et al. | |
| 5,048,301 A | 9/1991 | Sabin et al. | |
| 5,507,794 A | * 4/1996 | Allen | 607/114 |
| 5,984,953 A | 11/1999 | Sabin et al. | |
| 6,116,231 A | 9/2000 | Sabin et al. | |
| 6,393,843 B2 | * 5/2002 | Kohout | 126/263.08 |

FOREIGN PATENT DOCUMENTS

WO WO 00/69748 11/2000

OTHER PUBLICATIONS

SVI Swiss Star, "'Dream Steam'—One Way Pot for the Microwave," http://translate.google.com/translate_c?hl=en&u=http://www.svi–verpackung.ch/04–sStar/04–2., observed on Jul. 30, 2001.

"2000 WorldStar President's," http://www.packinfo–world.org/wpo/packnews/press/2000WorldStarPresident.s.html, Apr. 20, 2001.

"Award Winner, WPO Lauds 'Dream Steam'," http://209.15.189.141/printer_friendly.html?XP_TABLE=2001042301&XP9_PUB=packworld, Summit Publishing Company, May 2001.

"Cook–in package, Dream Steam Comes to the U.S.," Pat Reynolds, http://209.15.189.141/printer_friendly.html?XP—TABLE=2001052301&XP_PUB=packworld, Jun. 2001, pp. 1–3.

* cited by examiner

Primary Examiner—Henry Bennett
Assistant Examiner—James Barrow
(74) Attorney, Agent, or Firm—Fish & Richardson P.C.

(57) ABSTRACT

A disposable heating device is disclosed that includes a container having a first zone, a second zone and a third zone. A fuel is contained within the first zone and an oxidizing agent contained within the second zone. A first frangible separator disposed between the first zone and the second zone. The first frangible separator is manually operable to provide communication between the first zone and the second zone thereby defining a reaction zone. A second frangible separator is responsive to an exothermic chemical reaction within the reaction chamber. The second frangible separator is operable to provide communication between the reaction chamber and the third zone. Communication between the first zone and the second zone allows mixing of the fuel and the oxidizing agent to initiate an exothermic chemical reaction and an environmental parameter associated with the exothermic chemical reaction operates the second frangible separator.

35 Claims, 6 Drawing Sheets

HEAT PACK WITH EXPANSION CAPABILITY

FIELD OF THE INVENTION

The invention relates to heat packs, and more particularly to heat packs providing heat by exothermic chemical reactions.

BACKGROUND

Compact, self-heating devices that produce heat through exothermic chemical reactions are known in the art. For example, U.S. Pat. No. 4,397,315, Patel discloses a device having an outer envelope and an inner envelope, with the outer envelope containing sodium thiosulfate and the inner envelope containing ethylene glycol. The walls of the inner envelope are rupturable, allowing the contents of each envelope to mix.

U.S. Pat. No. 5,035,230, Steidl et al. discloses a heat pack having two compartments separated by a frangible seal. Potassium permanganate oxidizing agent coated with sodium silicate is provided in one zone of the heat pack, and aqueous ethylene glycol fuel is provided in the other zone. In operation of the device, the seal is compromised to allow the reactants to come in contact with each other.

U.S. Pat. No. 5,984,953, Sabin et al. discloses a disposable heat pack utilizing an exothermic chemical reaction. Moderation of the reaction is provided through the use of a preformed reversibly stiffenable gel that can be used to alter the rate of the exothermic chemical reaction.

U.S. Pat. No. 6,116,231, Sabin et al. discloses a liquid heat pack utilizing an exothermic chemical reaction to produce heat. Moderation of the reaction is provided by the use of a gelling agent, which can also give structural rigidity to the heat pack.

Heat packs of the types disclosed by Steidl et al. and Sabin et al., for example, have the potential to generate steam, if heat transfer to the heated subject is insufficiently rapid to prevent excessive temperature increase. Inasmuch as steam generation causes swelling and potentially could lead to rupture, such heaters are designed and sized to avoid excessive temperature. That, however, places limits on the range of conditions and applications under which the heater can operate.

SUMMARY OF THE INVENTION

An aspect of this invention is a disposable heater that is at once useful over a broader range of conditions yet is compact.

Another aspect of this invention is a disposable heater with improved robustness that provides the needed amounts of heat and temperature rise for a demanding application without "running away", that is, generating excessive pressure and temperature, when used in considerably less demanding application or situation. Thus, for example, the same disposable heater can be used for objects requiring a substantially different amount of heat or for heating under widely varying conditions, such as in the tropics and in winter conditions. In one broad aspect, a disposable heating device is disclosed that includes a container having a first zone, a second zone and a third zone. As used herein, "zone" means at least one chamber or compartment, and will be understood to include a plurality thereof. A fuel is contained within the first zone and an oxidizing agent is contained within the second zone. A first frangible separator is disposed between the first zone and the second zone. The first frangible separator is manually operable to provide communication between the first zone and the second zone thereby defining a reaction chamber or zone. A second frangible separator is responsive to an exothermic chemical reaction within the reaction chamber. The second frangible separator is operable to provide communication between the reaction chamber and the third zone. Communication between the first zone and the second zone allows mixing of the fuel and the oxidizing agent to initiate an exothermic chemical reaction. An environmental parameter associated with the exothermic chemical reaction operates the second frangible separator. The environmental parameter associated with the exothermic chemical reaction can be, for example, an elevated temperature or an elevated pressure or a combination of the two of them. The heater is designed such that, under most conditions of intended use, the second frangible separator will not be compromised. However, when there is a relatively very low rate of heat transfer out of the device, the second frangible separator will be compromised, thereby permitting steam to escape from the reaction chamber into the third zone. This removes water from the reaction chamber, slows dissolution of at least one reactant, and moderates the exothermic reaction. Simultaneously there is created another heat-transmitting zone to increase heat transfer and thereby moderate temperature rise. In some embodiments the additional heat transfer may be to the object being heated. In other embodiments the additional heat transfer may be to the surrounding environment, as persons skilled in the art can readily design. For embodiments of either type, the heating device may include a heat sink thermally coupled to the third zone. A preferred heat sink is a phase change material. If desired, the phase change material can be thermally coupled to the object being heated so as to prolong the time of heating. Preferably the third zone is an expandable zone that balloons when the second frangible seal is compromised so that prior to use and under most conditions of use the third zone occupies minimal space. The control provided by the third zone can be used in conjunction with other controls. Preferably the latter are sufficient to prevent compromise of the second frangible seal under almost all conditions. For example, the disposable heating device may also include a non-fuel gelling agent solution in at least one of the zones, wherein communication between the gelling agent and the reaction chamber initiates gelation of the gelling agent to produce a non-fuel gel that moderates the rate of the reaction independently of dissolution of the gelling agent. A sufficient amount of gelling agent may be provided to produce gel rapidly enough to prevent a temperature associated with the exothermic chemical reaction from exceeding a predetermined maximum value under expected conditions. Embodiments of the disposable heating device of this invention include a preformed stiffenable gel and a vaporizable solvent in the first zone. Oxidizing agent may be embedded and dispersed throughout the second zone in a dissolvable binding agent that dissolves during the exothermic chemical reaction to controllably expose the oxidizing agent at a predetermined rate. The vaporizable solvent may be selected to vaporize when a temperature associated with the exothermic chemical reaction reaches a predetermined maximum value, thereby causing stiffening of the gel to moderate the exothermic chemical reaction. A sufficient amount of preformed stiffenable gel may be included so as to prevent the temperature associated with the exothermic chemical reaction from exceeding the predetermined maximum value in most cases.

As stated earlier, the disposable heating device may include a plurality of compartments as the first zone and/or a plurality of compartments as the second zone. The disposable heating device can be conformable to a shape defined by its surroundings. In preferred embodiments, the material from which the device is constructed is resistant to the exothermic chemical reaction. The material can be, for example, a polymeric material. The exothermic chemical reaction can be a reduction-oxidation type of reaction. The oxidizing agent can be potassium permanganate and the fuel can be an oxidizable organic compound. The disposable heating device can include a valve coupled to the container and operable to provide communication between either the first zone, the second zone, or the third zone and atmosphere. The valve can be responsive to at least one of either temperature or pressure. The disposable heating device can be of modular construction, including two or more complete heating-device modules physically connected as a single unit, wherein each module is isolated from an adjacent module by a separator disposed there between. The second frangible separator can include frangible portions and securely sealed (non-frangible) portions, which may be aligned in an alternating pattern. Where multiple first frangible separators are used, each can be independently operable. The first zone and the second zone can be in thermal contact with a product to be heated, such as food, drink, with a body part of a surgical patient or of a patient undergoing therapy, or with an article of clothing or footwear.

In another broad aspect, a disposable heating device is disclosed that includes a flexible upper sheet, a flexible lower sheet attached to the upper sheet at edges thereby defining a compartment. A manually operable first frangible separator is disposed within the compartment to define a first zone containing a fuel and a second zone containing an oxidizing agent. A second frangible separator, responsive to an exothermic chemical reaction, is disposed within the compartment to provide an interface between at least one of either the first zone or the second zone and a third zone. Manual operation of the first frangible separator allows communication between the first zone and the second zone to create a reaction zone and to initiate an exothermic chemical reaction. The exothermic chemical reaction operates the second frangible separator to provide communication between the reaction zone (at least one of either the first zone or the second zone) and the third zone. Operation of the second frangible separator can be in response to, for example, an elevated pressure or an elevated temperature associated with the exothermic chemical reaction. The upper sheet and the lower sheet can each be conformable to a shape defined by their surroundings. The upper sheet and the lower sheet can be fabricated using a material that is resistant to the exothermic chemical reaction, for example, a polymeric material. The first zone and the second zone can be in thermal contact with a product to be heated. Gelling agents, preformed gels, or heat sink material can be included, as discussed above. The second frangible separator can include a plurality of frangible portions and a plurality of non-frangible portions. The frangible portions and non-frangible portions can be linearly aligned in an alternating manner across the second frangible separator.

In yet another broad aspect, a disposable heating device is disclosed that includes a reaction chamber defining an initial internal volume for initiating an exothermic chemical reaction therein, an expansion chamber adjacent to the reaction chamber and a frangible seal disposed between the reaction chamber and the expansion chamber, the frangible seal being operable in response to the exothermic chemical reaction. Operation of the frangible seal establishes communication between the reaction chamber (in preferred embodiments, the reaction chamber is created through combining a first zone and a second zone) and the expansion chamber thereby defining an increased internal volume for containing the exothermic chemical reaction. Operation of the frangible seal causes a reduction of pressure associated with the exothermic chemical reaction. The increased internal volume through the addition of the third zone can be 101% to approximately 200% greater than the initial internal volume or, preferably, approximately 110% to 150% and even more preferably 125% to 150% greater than the initial internal volume. The frangible seal can be operable in response to an elevated temperature associated with the exothermic chemical reaction. The frangible seal can be operable in response to an elevated pressure associated with the exothermic chemical reaction. A heat sink can be provided within, or, in thermal contact with, the expansion chamber (i.e., the third zone). A valve can be coupled to the reaction chamber, the valve being responsive to at least one of either pressure or temperature, and being operable to provide communication between the reaction chamber and atmosphere.

In still another broad aspect, a method of heating a product is disclosed that includes providing a heating device in thermal contact with the product and compromising a first frangible separator to establish communication between a first zone and a second zone, thereby initiating an exothermic chemical reaction therein and subsequent heating of the product. The heating device comprises a container having a first zone, a second zone and a third zone. A fuel is contained within the first zone, and an oxidizing agent is contained within the second zone. A first frangible separator is disposed between the first zone and the second zone, the first frangible separator being manually operable to provide communication between the first zone and the second zone. A second frangible separator, responsive to temperature and/or pressure, is operable to provide communication either between the third zone and the first zone, the second zone, or both. Communication between the first zone and the second zone allows mixing of the fuel and the oxidizing agent to create an exothermic chemical reaction generating vapor in the first zone and the second zone. A pressure and a temperature associated with generating the vapor operates the second frangible separator to allow the vapor to move into the third zone. The product to be heated can be, for example, food, drink, a body part of a surgical patient, clothing or footwear. The heating device also can include a plurality of containers, as described above, and the method can further include compromising at least one additional first frangible separator to initiate a second exothermic chemical reaction.

Depending on the embodiment selected, one or more of the following advantages may be realized. In all cases, rupture of the heat pack is avoided, and volumetric expansion is controlled both by moderation of the exothermic chemical reaction and increased transfer of heat out of the device. In cases in which the area available for transfer of heat to the object to be heated is limited, heating efficiency is improved by providing a third zone that discharges heat to the environment but does not contain reactants. Less reactant is needed. Heat packs can be designed to generate heat faster under maximum intended load without risking rupture under a much lower load. Heat packs can be made smaller by providing the third zone in a collapsed state. In some implementations, the third zone can be thermally coupled to the product to be heated. In other implementations, the third zone can be thermally isolated from the product to be heated.

The invention is in similar fields as inventions described in and claimed by, for example, U.S. Pat. No. 5,035,230, Steidl et al., U.S. Pat. No. 5,984,953, Sabin et al., and U.S. Pat. No. 6,116,231, Sabin et al., each of which is incorporated by reference in their entirety.

As used herein, the following definitions should be understood in such a manner so as not to limit the scope of the application. The term "expansion" used with reference to heat packs should be understood to include swelling of heat packs and increases in internal volume associated with particular compartments of heat packs. The term "run away" is used to describe any uncontrolled event or any event that might result in an unexpected or undesirable outcome. The term "environmental parameter" should be understood to include temperature, pressure, a combination of temperature and pressure, or volumetric expansion. The phrase "static" is used to describe a heat pack that has not been activated (i.e., its first frangible separator has not been compromised).

All publications, patent applications, patents, and other references mentioned herein are incorporated by reference in their entirety. In case of conflict, the present specification will control. In addition, the apparatus, methods, and techniques described herein are illustrative only and are not intended to be limiting. The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

Like reference symbols in the various drawings indicate like elements.

DETAILED DESCRIPTION

Disposable heat packs according to the invention operate on a principle of evolution of the heat of reaction that is created when one chemical entity contacts another. In a preferred embodiment for use in this invention, contact between an oxidizing agent and a compatible reducing agent (fuel) results in an exothermic chemical reaction. The exothermic chemical reaction can be, for example, an oxidation/reduction reaction. Heat packs include a reaction chamber with an initial volume within which the exothermic chemical reaction can be initiated. Heat packs according to this invention include also an expansion chamber adjacent to the reaction chamber and isolated from the reaction chamber by a frangible separator disposed there between. The frangible separator operates to provide hydraulic communication between the reaction chamber and the expansion chamber in response to the exothermic chemical reaction, thereby establishing an increased internal volume for containing the exothermic chemical reaction. Heat packs utilizing oxidation/reduction reactions are disclosed in, for example, U.S. Pat. No. 5,035,230, Steidl et al.

Figure 1:
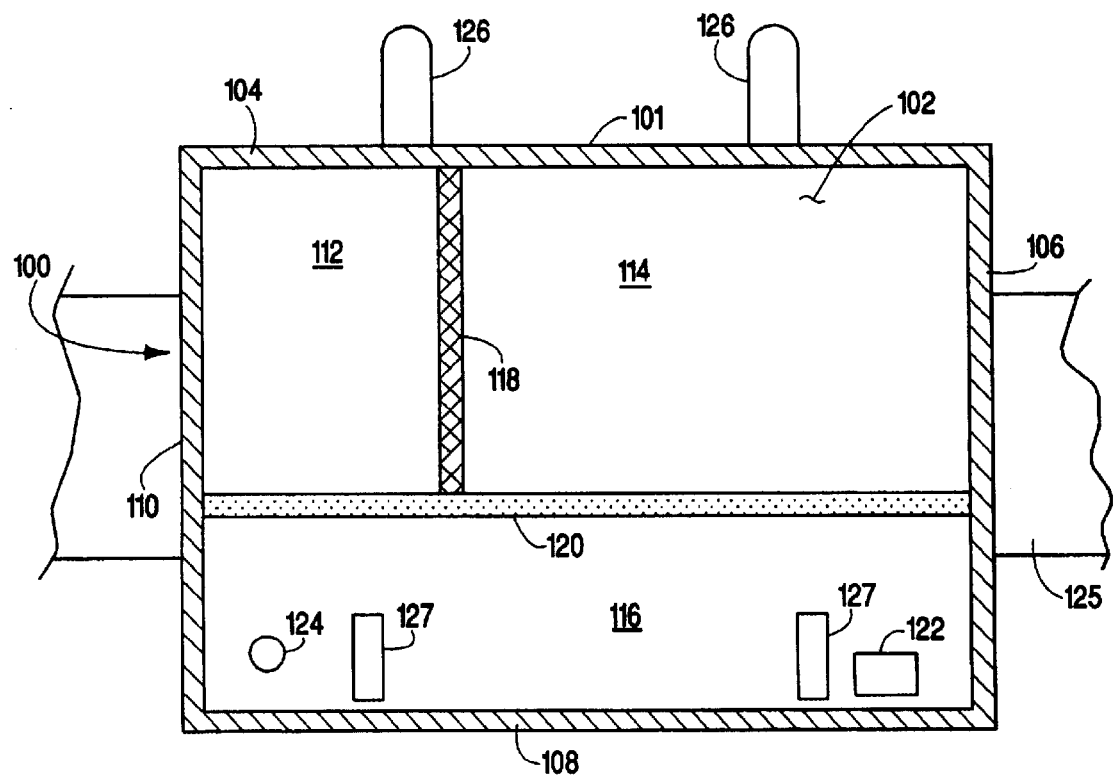
FIG. 1 shows an overhead planar view of a particular embodiment of a heat pack.

Referring to FIG. 1, there is displayed an overhead planar view of a particular embodiment of a disposable heat pack 100. Heat pack 100 comprises container 101 having upper sheet 102 and a lower sheet (not shown). The sheets are sealed together at the edges by edge seals, 104, 106, 108 and 110. These edge seals are made so that they cannot be readily opened or otherwise compromised by a consumer.

Container 101 is internally divided into first zone 112, second zone 114 and third zone 116. In a static condition, first zone 112 contains a fuel and second zone 114 contains an oxidizing agent. First frangible separator 118 is disposed between first zone 112 and second zone 114. First frangible separator 118 is preferably made so that a consumer can manually compromise it.

Third zone 116 is positioned adjacent to first zone 112 and second zone 114. Third zone 116 is isolated from first zone 112 and second zone 114 by second frangible separator 120. Second frangible separator 120 is responsive to an exothermic chemical reaction that is initiated when first frangible separator 118 is compromised allowing the fuel to contact the oxidizing agent. Second frangible separator 120 can be compromised, for example, by an increase of temperature, pressure or both within heat pack 100 resulting from the exothermic chemical reaction. When second frangible separator 120 is compromised, an increased internal volume is provided in heat pack 100 for containing the exothermic chemical reaction.

Several oxidizing agents are capable of generating suitable amounts of heat upon reaction with a corresponding fuel. Typical oxidizing agents include, for example, alkali metal salts of manganese and chromium. These include such compounds as potassium permanganate, and potassium chromate. Other suitable oxidizing agents are pyridnium dichromate, ruthenium tetroxide and chromic acid, as well as a host of other oxidizing agents known to those skilled in the art.

Suitable fuels include, for example, organic compounds. Particularly well-suited organic compounds are alcohols. Oxidizing agents described herein can easily oxidize alcohols to carbonyl-containing compounds. Preferable alcohols include primary alcohols, and polyols that contain at least two hydroxyl groups. Polyols can be readily oxidized to aldehydes and carboxylic acids. Oxidation of polyols is typically accompanied by the creation of significant amounts of heat. Glycerine is among other suitable fuels known to those of skill in the art.

Fuels and oxidizing agents used in a particular heat pack should be complementary. Suitable choices can include any combination that is able to provide the desired characteristics as outlined herein, meet government safety standards, and be compact. For most applications, oxidizing agents and fuels should conform to applicable government standards in case any discharge into the environment occurs, accidentally or otherwise. In one of the preferred embodiments, the oxidizing agent comprises potassium permanganate and the fuel comprises glycerine.

As an option, heat sink 122 can be thermally coupled to third zone 116. Heat sink 122 can be positioned within third zone 116 or outside but near third zone 116 so that adequate thermal coupling exists. Heat sink 122 can be, for example, a phase change material, or, more generally, a material that has a high-heat absorbing capacity.

Suitable phase change materials for particular heat sink applications can include, for example, paraffin, naphthalene, sulphur, hydrated calcium chloride, bromocamphor, cetyl alcohol, cyanimide, eleudic acid, lauric acid, hydrated sodium silicate, sodium thiosulfate pentahydrate, disodium phosphate, hydrated sodium carbonate, hydrated calcium nitrate, Glauber's salt, potassium, sodium, magnesium acetate and wax.

Phase change materials can absorb some sensible heat, which results in an increase in the temperature of heat sink 122. However, phase change materials typically absorb more significant amounts of heat during a change of phase (e.g., a change from a solid phase to a liquid phase, or a change from a liquid phase to a vapor phase, or changes of phase within a state, such as the solid state). The temperature of a phase change material typically remains relatively constant throughout the phase change, despite the large amount of heat that the phase change material can absorb.

A preferred embodiment includes a phase change material that is chosen so that it changes from a solid to a liquid in a useful temperature range depending on the particular application. However, a phase change material that changes from a liquid to a vapor also can be used. A liquid could be isolated from direct contact with, but thermally coupled to third zone 116, for example, by containing the liquid in a packet that is within the third zone. Phase change material vapor, if generated, could be vented so that it carries heat away from third zone 116 and the heat pack. A phase change material with a specific melting point may be used to limit heat pack operating temperatures to a desired maximum value without generating vapor.

A phase change material should be selected so that it changes phase at a temperature that is higher than the highest expected ambient temperature of the product to be heated, but less than a predictable maximum temperature that a heat pack would be expected to reach during operation of the device. If a heat pack exceeds the normal operating temperature for any reason, the heat sink can absorb a large amount of heat in a phase transition, and moderate further "run away" behavior.

Heat sinks also can be materials having high-heat absorbing capabilities without necessarily changing phase. Exemplary materials include cyanimide, ethyl alcohol, ethyl ether, glycol, isoamyl alcohol, isobutyl alcohol, lithium hydride, methyl alcohol, sodium acetate, water, ethylene glycol, paraffin wax and other heat absorbing materials known to those of skill in the art.

If heat sink material can exist in either a liquid or a vapor phase, it may be necessary to package the heat sink material to prevent direct contact with contents inside the heat pack. For example, small individual packages of heat sink material can be scattered throughout the third zone of the heat pack when heat sink material cannot be in direct contact with the inside of the third zone. Alternatively, heat sink material can be placed in a single package having a relatively large surface area that is thermally coupled to the heat pack.

The third zone of heat pack container 101 is preferably a collapsed, balloonable structure. As depicted, the entire container 101 is constructed of thin, flexible, thermally conductive polymeric material to form a hermetically sealed, substantially planar envelope. In one preferred embodiment, the material is a metal foil, such as one composed substantially of aluminum or copper, or a metallized plastic film such as aluminized polyester, for example MYLAR®. The shape of a container can typically conform to various shapes as required by its particular surroundings. Additional container constructions and configurations are disclosed in U.S. Pat. No. 5,984,953, Sabin et al.

Either the oxidizing agent or the fuel/gelling agent or any solvent that is chosen for inclusion in the heat pack should not deleteriously affect the material that the container is made of. The material also should be capable of withstanding high temperatures, at least up to the maximum temperature the container is expected to reach during operation. Such materials include polyethylene, polypropylene, polyester, such as MYLAR®, aluminum, aluminized polymer film, and other conventional plastic or other packaging materials suitable for containing heated liquids such as rubber, vinyl, vinyl-coated fabric and polyethylene. The material thickness typically ranges from about 0.02 mm to about 0.1 mm, although other material thicknesses may be found suitable for certain applications.

In a particular embodiment, third zone 116 includes a vent 124 to provide communication from third zone 116 to atmosphere. Vent 124 can be responsive, for example, to an elevation in temperature, pressure or a combination of temperature and pressure. If the temperature and/or pressure inside container 101 reach a predetermined threshold value, vent 124 can open to controllably release a portion of vapor from heat pack 100 to the surrounding atmosphere. The vent closes after releasing a desired amount of vapor from container 101. Vent 124 should be designed to relieve a sufficient amount of pressure from the heat pack to prevent undesirable rupturing, for example, of the container and/or edge seals.

Alternate arrangements could include a vent coupled to either the first zone or the second zone. Additionally, multiple vents may be provided in various areas of container 101.

Edge seals 104, 106, 108 and 110 can be bonded together by using any suitable technique known to those with ordinary skill in the art. Suitable techniques include soldering, heat sealing, ultrasonic welding, fold sealing and by using adhesives.

During fabrication of heat pack 100, container 101 preferably comprises an open end or side at each of zones 112, 114, 116 for introducing fuel, reducing agent, heat sink material, other solvents, etc., as required. The other sides or edges can be sealed prior to introducing these items. After introducing these items, the open sides can be sealed to make container 101 fluid-tight and airtight. The size and shape of container 101, as well as the juxtaposition and configuration of zones within the container will vary according to the specific application for which the heat pack is intended to be used. Accordingly, alternative assembly procedures may be required to properly assemble heat packs for different applications. The scope of the invention is not limited by the arrangement of zones within the container.

After assembly and prior to use, the heat pack 100 is in a static condition, in which the first zone contains a reducing agent (i.e., a fuel) and the second zone contains an oxidizing agent. The third zone can be empty. Alternatively, the third zone can include a heat sink.

Communication between the first and second zones allows the oxidizing agent to contact the fuel and thereby initiate an exothermic chemical reaction. The exothermic chemical reaction causes the temperature of the heat pack to rise. Heat can be transmitted by conduction and convection through the heat pack to the exterior surfaces of the device, where it can be further transmitted to other bodies, according to specific applications for which the heat pack is employed. A characteristic feature of the heat pack is the attainment of an operating temperature which is measured on its surface. Typical heat pack operating temperatures can vary from about 20° F. above ambient temperature to about 120° F. above ambient temperature.

To initiate the exothermic chemical reaction, the fuel and the oxidizing agent must come into contact with each other. This is accomplished by opening, selectively perforating, rupturing or otherwise compromising the first frangible separator between the fuel and oxidizing agent containing zones, so that the oxidation/reaction partners can contact each other. In a preferred embodiment, the oxidizing agent is transferred into the first zone to contact the fuel. However, it is also contemplated that the fuel could be transferred into the second zone to contact the oxidizing agent. Either zone may contain a gelling agent for moderating the exothermic chemical reaction.

Pressure can be applied either against or along the first frangible separator to selectively rupture, perforate, or otherwise compromise the first frangible separator, while leaving the outer surfaces of the container, the edge seals and the second frangible separator intact. The first frangible separator can be comprised utilizing any of a number of functional configurations. In a preferred embodiment, the first frangible separator comprises a brittle or weakened wall, such as a portion separator 118, which is manually separable. In another embodiment, the first frangible separator 118 can be compromised by the use of pull tabs (not shown). When pulled, the pull tabs compromise the first frangible separator to establish communication between the first zone and the second zone. In another embodiment, the first frangible separator comprises a hole with a stopper, which is removable when pressure is applied to it. In yet another embodiment, the first frangible separator comprises a wall having a plurality of perforations, which can rupture under an applied pressure. Alternatively, the first frangible separator can consist of a movable disk or cap, pierced or otherwise, or a valve, such as a frangible valve. Alternatively, the first frangible separator can be configured to form one or more fissures when the first frangible separator is subjected to an externally applied pressure. The fissures can extend inwardly from the edges or perimeter of the first frangible separator, or they can be located intermediate the edges or perimeter of the first frangible separator. Most preferably, the first frangible separator comprises a wall having weakened or thin areas, which rupture when pressure is applied. Any adequate means for compromising the first frangible separator can be used. The second frangible separator can be fabricated using techniques known in the industry, such as heat sealing or using adhesives. Persons skilled in the art will recognize various other possibilities.

When the first frangible separator is compromised, an internal reaction chamber is defined within which an exothermic chemical reaction is initiated. The exothermic chemical reaction is initiated when the fuel and the oxidizing agent contact each other within the reaction chamber. The exothermic chemical reaction can result in an increase in temperature and a generation of vapor within the reaction chamber. The generation of vapor can result in an elevated pressure inside the reaction chamber.

The second frangible separator can open in response to the exothermic chemical reaction. For example, the second frangible separator could open in response to an increase in temperature, or an increase in internal pressure, or by a combination of increases in temperature and internal pressure resulting from the exothermic chemical reaction. The second frangible separator can open in response to a swelling, for example, of the reaction chamber. The second frangible separator can optionally include provisions for hand operation.

The use of a chemical reaction to generate heat, if not moderated, can lead to a very rapid rate of heat production, and a correspondingly rapid temperature rise. A rapid temperature rise is not necessarily a desirable heating profile for every application. Moreover, it can be hazardous. Therefore, it may be desirable to moderate the production of heat in a heat pack. Heat packs addressing these issues are disclosed in U.S. Pat. No. 5,035,230, Steidl et al. and U.S. Pat. No. 6,116,231, Sabin et al.

In a particular embodiment, heat packs can include a preformed stiffenable gel and a vaporizable solvent in the first zone and oxidizing agent embedded and dispersed throughout the second zone in a dissolvable binding agent. The dissolvable binding agent can dissolve during the exothermic chemical reaction to controllably expose the oxidizing agent at a predetermined rate. The vaporizable solvent can vaporize when a temperature associated with the exothermic chemical reaction reaches a predetermined maximum value, thereby causing stiffening of the gel to moderate the chemical reaction. A sufficient amount of preformed stiffenable gel is typically provided to prevent the temperature associated with the exothermic chemical reaction from exceeding a predetermined maximum value.

In another embodiment, a non-fuel gelling agent solution is provided in at least one of either the first zone, the second zone or the third zone. Contact between the gelling agent and the exothermic chemical reaction can initiate gelation of the gelling agent to produce a non-fuel gel that moderates the rate of the reaction independently of dissolution of the gelling agent. A sufficient amount of gelling agent is typically provided to produce gel rapidly enough to prevent a temperature associated with the exothermic chemical reaction from exceeding a predetermined maximum value.

Figure 2A:
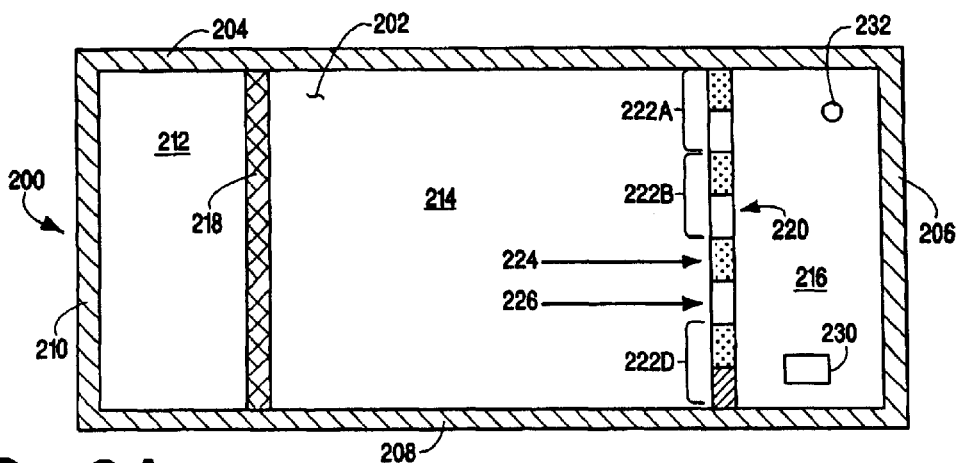
FIGS. 2A through 2C show planar views of a particular embodiment of a heat pack in various stages of operation.

An alternative embodiment of a heat pack is illustrated in FIG. 2A. Heat pack 200 includes upper sheet 202, lower sheet (not shown) and four edge seals 204, 206, 208 and 210. Heat pack 200 is internally divided into first zone 212, second zone 214 and third zone 216. In this embodiment, not only third zone 216, but the entire device is flexible and in a collapsed state. In a static condition, first zone 212 contains a fuel and second zone 214 contains an oxidizing agent. First frangible separator 218 is disposed from edge seal 204 to edge seal 208.

Second frangible separator 220 is disposed substantially parallel to first frangible separator 218 also from edge seal 204 to edge seal 208. Second frangible separator 220 includes multiple sections 222A, 222B . . . 222D linearly arranged. Each section 222A, 222B . . . 222D includes a frangible portion 224 and a non-frangible portion 226. Each frangible portion 224 can be implemented as a weakened seal, for example, a seal created using meltable adhesives, or weak adhesives. Alternatively, frangible portions 224 could include a temporary interference type seal that is easily opened. Non-frangible portions 226 are more securely sealed than frangible portions 224.

Figure 2B:
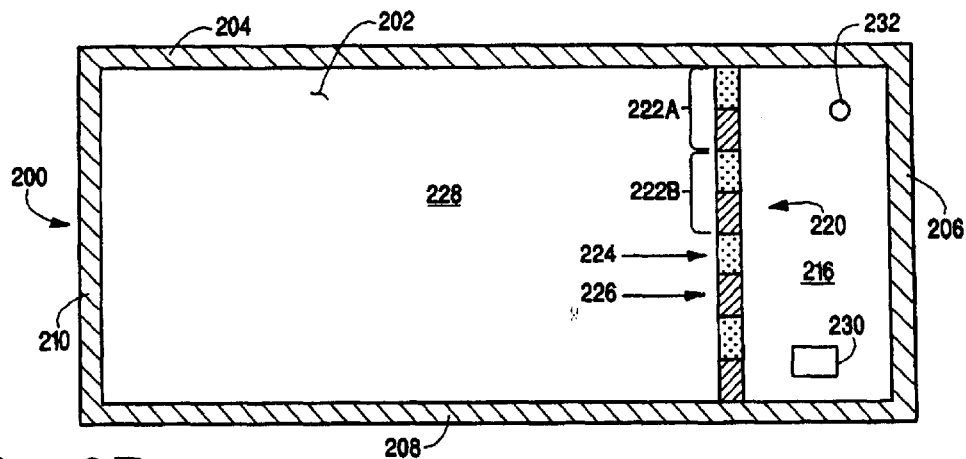

Referring to FIG. 2B, heat pack 200 is shown immediately after first frangible separator 218 has been compromised. First zone 212 and second zone 214 are in communication with each other and define reaction chamber 228. The reaction chamber is isolated from third zone 216 by second frangible separator 220. The fuel contacts the oxidizing agent within reaction chamber 228 to initiate an exothermic chemical reaction therein.

Figure 2C:
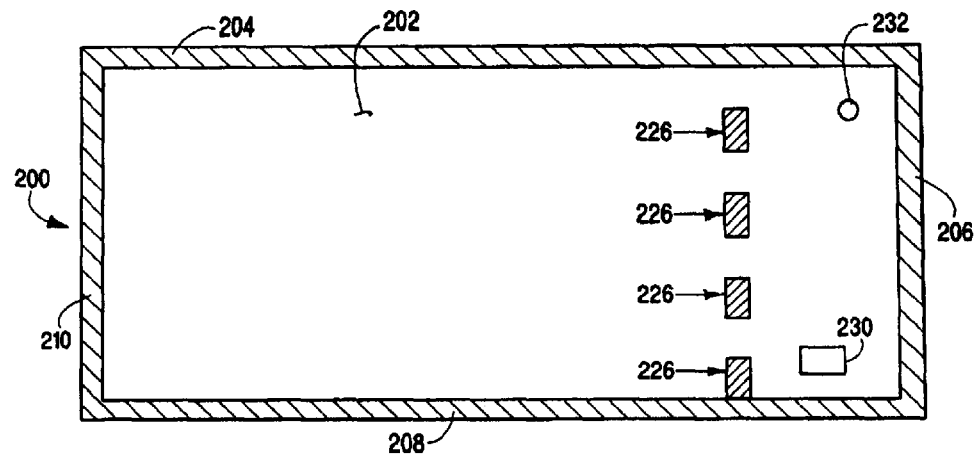

Referring to FIG. 2C, heat pack 200 is shown immediately after frangible portions 224 of second frangible separator 220 are compromised by the exothermic chemical reaction. The opening of frangible portions 224 can be, for example, in response to a temperature or a pressure associated with the exothermic chemical reaction. Non-frangible portions 226 are still intact. They do not operate responsive to the exothermic chemical reaction. This construction allows vapor to migrate from the reaction chamber 228 into third zone 216 while simultaneously preventing solid fuel or solid oxidizing agent from undesirably moving into third zone 216.

Each frangible portion 224 should be wide enough to ensure its proper opening under expected heat pack 200 operating conditions. If frangible portions 224 are too narrow, it may be difficult for them to open.

Typically, a heat pack includes between approximately two and ten sections 222A, 222B . . . 222D. More preferably, a heat pack includes between approximately three and seven sections 222A, 222B . . . 222D.

Heat pack 200 includes heat sink 230 inside the third zone. If the heat sink is not secured in place, frangible portions 224 of second frangible separator 220 should be narrow enough to prevent the undesirable passage of the heat sink into the reaction chamber when the frangible portions are compromised.

Vent 232 provides communication between the third zone and atmosphere in the event that dangerously high pressures are created by the exothermic chemical reaction within the heat pack. Vent 232 can be designed to rapidly release or slowly release excessive pressure.

An alternative arrangement of a heat pack could include a second frangible separator 120 disposed between first zone 112 and third zone 116 only.

Figure 3:
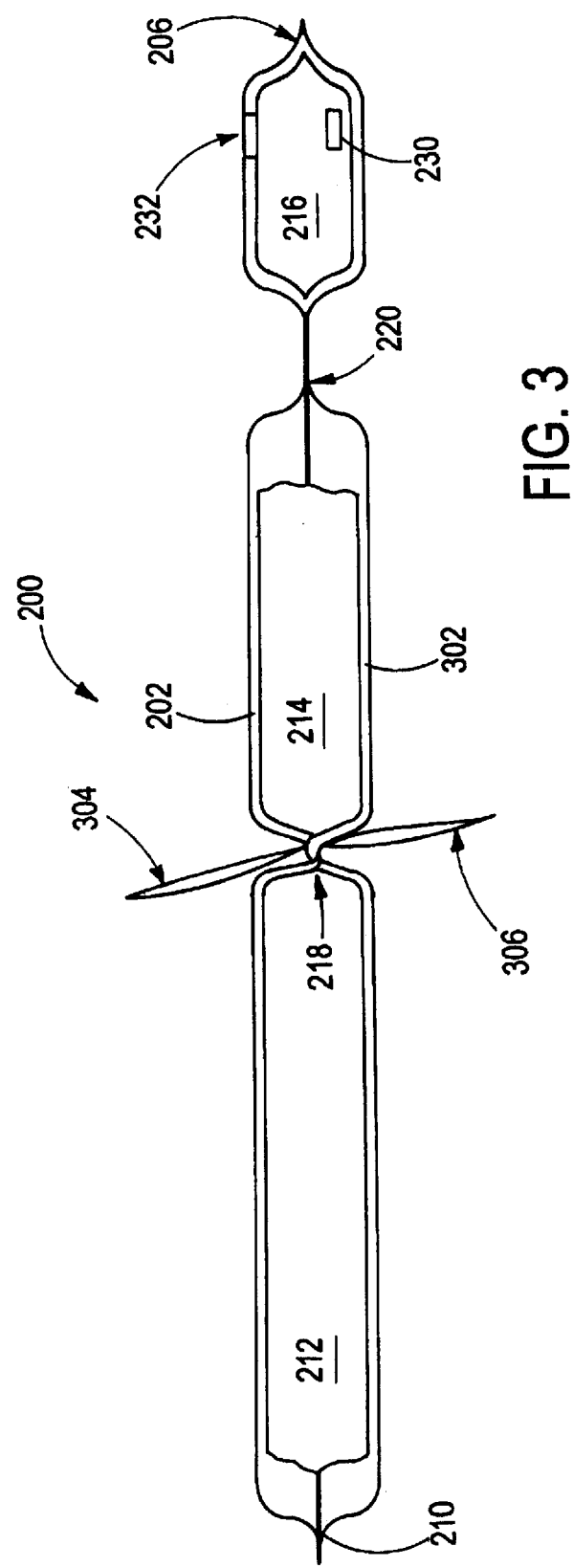
FIG. 3 shows a sectional view of the heat pack of FIG. 2A.

FIG. 3 shows a section view of the particular embodiment of FIG. 2A, with the inclusion of the lower sheet 302. Also shown is an optional feature of pull-tabs 304 and 306 coupled to first frangible separator 218. When pulled, the pull-tabs can compromise the first frangible separator and provide fluid communication between first zone 212 and second zone 214, thereby initiating an exothermic chemical reaction. The exothermic chemical reaction can then cause the second frangible separator 220 to open.

Figure 4A:
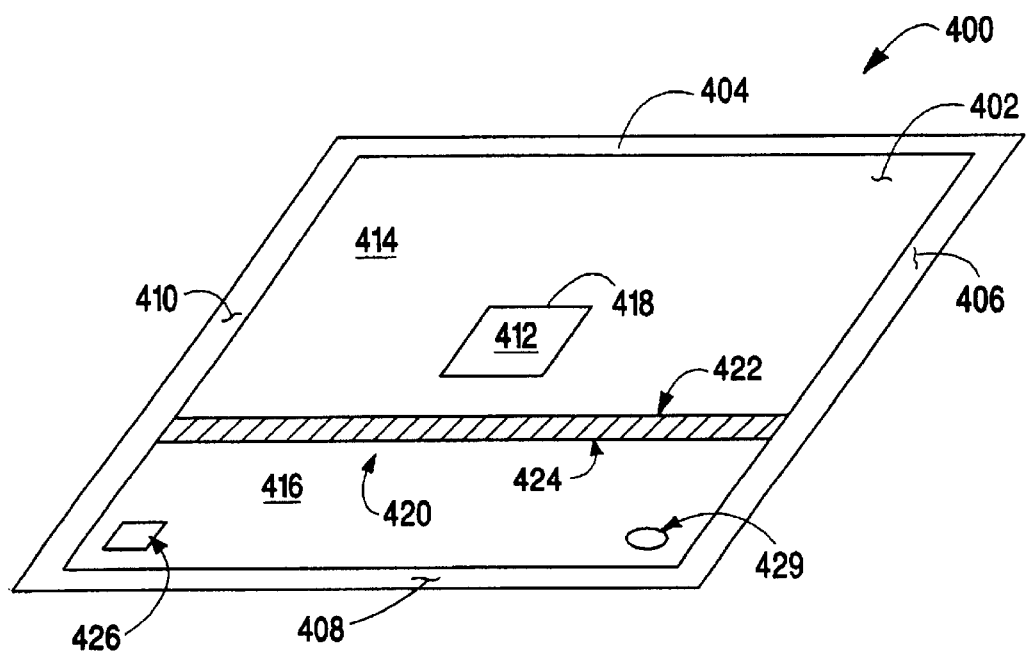
FIGS. 4A and 4B shows perspective views of alternative heat pack arrangements.

Referring now to FIG. 4A, a particular embodiment of a heat pack 400 includes an upper sheet 402 attached to a lower sheet (not shown) at edge seals 404, 406, 408, 410 to define container. The container is internally divided into first zone 412, second zone 414 and third zone 416.

In a static condition, first zone 412 contains a fuel and second zone 414 contains an oxidizing agent. The first zone is isolated from the second zone by first frangible separator 418 disposed between the zones. First zone 412 is a sealed packet (or a rupturable blister) containing a fuel. Applying a pressure to the first zone can rupture the sealed packet. First zone 412 and second zone 414 are isolated from third zone 416 by second frangible separator 420.

The second frangible separator includes frangible portions 422 and non-frangible portions 424 arranged linearly and positioned in an alternating fashion.

Heat sink 426 is in thermal contact with third zone 416 and a vent 429 also is coupled to the third zone 416.

Figure 4B:
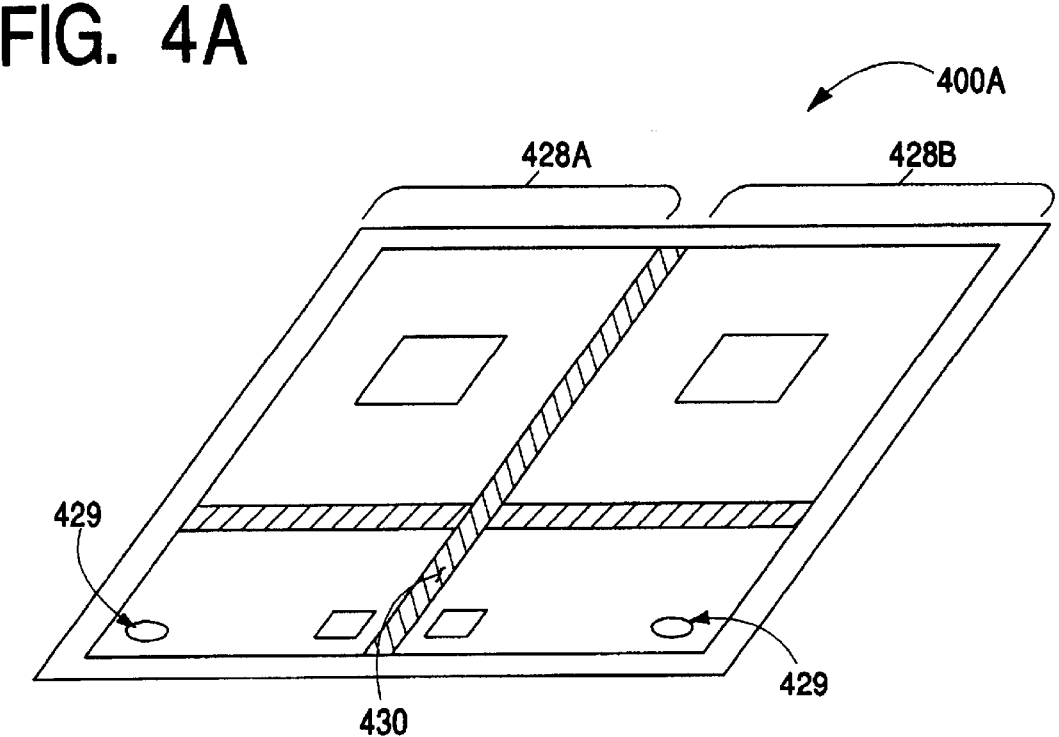

Referring to FIG. 4B, a particular embodiment of a heat pack 400A includes two integral heating devices 428A, 428B positioned side by side and isolated from each other by a non-frangible seal 430 disposed there between. Each heating device is independently operable to provide incremental control of heat generation associated with the heat pack. Certain implementations could include additional heating devices 428 arranged adjacent to each other, with each heating device isolated from adjacent heating devices by associated non-frangible seals.

Figure 5A:
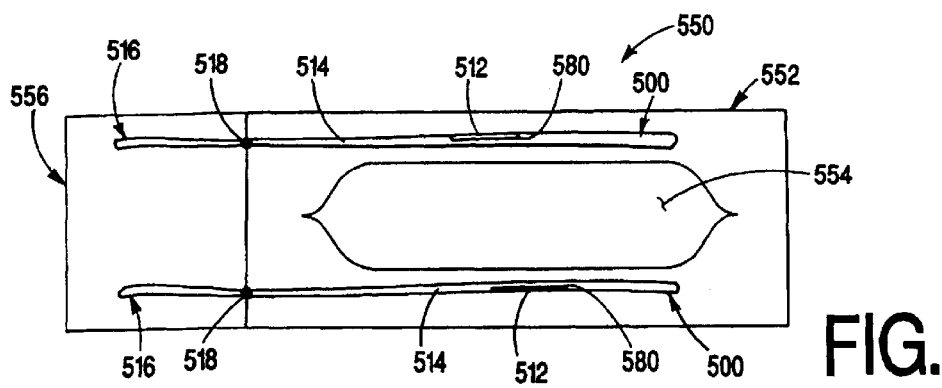
FIGS. 5A through 5C show sectional views of a particular embodiment of a food carton that can be fabricated using the inventive heat packs.

FIG. 5A illustrates a cross sectional cutaway view of particular embodiment of a self-heating container 550 of food. A disposable carton 552 contains a packet 554 of food. Two heat packs 500 are positioned within the carton and are at least partially thermally coupled to packet 554. Each heat pack includes a first zone 512 containing a fuel, second zone 514 containing an oxidizing agent and a third zone 516. The first and second zones of each heat pack are positioned above and below food packet 554, respectively. Third zones 516 are positioned at least partially outside the carton and acts as an expansion chamber for the expansion of vapors associated with an exothermic chemical reaction. Third zones 516 are isolated from the first and second zones by second frangible separators 518 that are responsive to an exothermic chemical reaction.

The heat pack 550 and carton 552 are designed such that, when frangible separators 518 are compromised, third zones 516 expand outwardly and dump heat to the environment. Heat pack 550 can be designed such that initially third zones 516 are at least partially outside carton 552, as depicted. Alternatively, heat pack 550 can be designed such that initially third zones 516 are entirely within carton 552 but expand to be at least partially outside. The expansion may include unfolding. Certain implementations of this embodiment include an extension 556 from the carton for containing the third zones of the heat packs. In the embodiment shown in FIG. 5A, third zones 516 are intended to be thermally isolated from the product to be heated. As shown, isolation from the packet of food is achieved by positioning third zones 516 within extension 556, which is preferably open to the environment.

Applying pressure to the first zones through the carton can rupture first frangible separators 580. This allows the fuel to contact the oxidizing agent thereby initiating an exothermic chemical reaction.

Figure 5B:
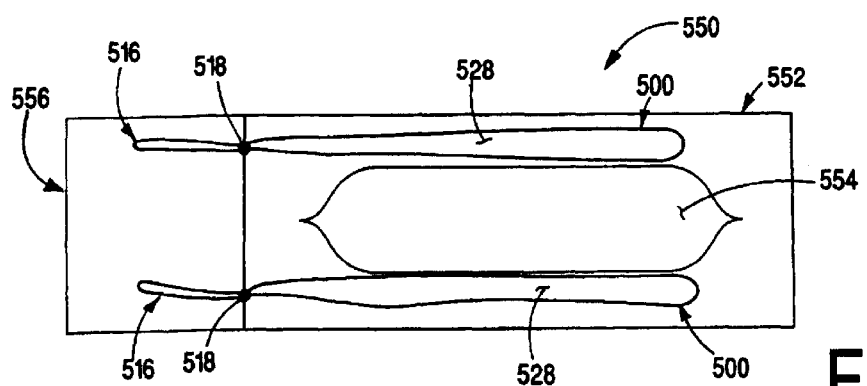

FIG. 5B illustrates the self-heating container of food after the first frangible separators 580 have been ruptured. The first zones and the second zones have thereby been combined to define reaction chambers 528 in each heat pack. The reaction chambers each have an internal volume for containing the respective reactions. As the reactions progress, heat is generated within the reaction chambers the reaction chambers can swell with an associated increased pressure within the reaction chambers. In certain implementations, some swelling is desirable to facilitate establishing good thermal contact between the heat packs and the packet of food. Excessive swelling, however, can be undesirable, due to the potential for the heat pack to rupture.

Figure 5C:
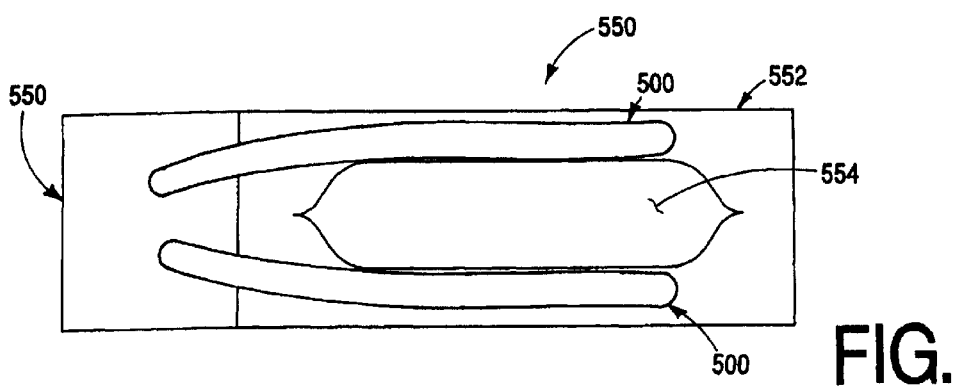

As the heat packs heat up and swell, a predetermined actuation point may eventually be reached, and the second 518 frangible separators open, as shown in FIG. 5C. Opening of the second frangible separators increases the amount of internal volume available to contain each exothermic chemical reaction and results in a reduction of internal pressure within each heat pack, thereby minimizing the possibility of heat pack rupturing. Heat is transferred to the environment, and water is removed from the reaction.

Heat packs can be adapted to be used in medical applications, such as during human or veterinary surgery. During surgery, core body temperatures can drop to undesirable levels. Heat pack can be used to warm patients. For these and other applications, heat packs can be provided within a thermally conductive package having either an adjustable or fixed shape. Exemplary packages can have a variety of possible shapes and sizes, and can include, for example, cartons, sleeves, wraps, and boxes. Such heat packs preferably include a fastening device, which allow the initial positioning of a heat pack, for example, onto a limb 125 (FIG. 1). Subsequent activation of the device can take place without further positional adjustment. Suitable fastening devices include straps, adhesives, or reusable strips, such as VELCRO® strips 126. 127 (FIG. 1). Certain surgical applications can include heat packs designed as a sleeve, which is dimensioned to be place around a limb 125 (FIG. 1), such as the leg of a human, horse, dog, cat or any other animal for which surgery may be carried out. Alternatively, flat heat packs can be inserted into a fabric sleeve or wrap. Desirably, the sleeve diameter is adjustable, permitting the use of the same sleeve on a variety of patients. Alternatively, a heat pack can be designed as a pad, allowing broad body surfaces such as the back or chest of a human or animal to be heated.

Figure 6:
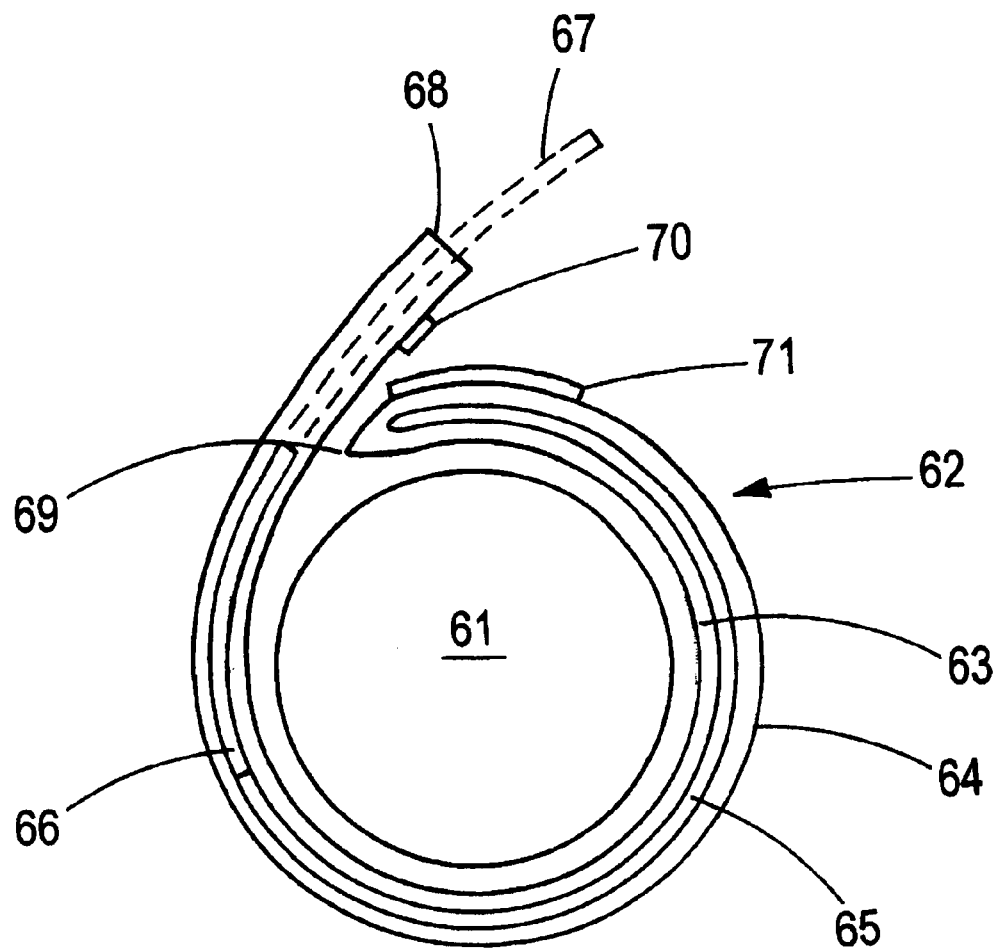
FIG. 6 shows a cross sectional view of a sleeve containing a heat pack according to this invention wrapped around and secured to a product.

FIG. 6 shows a product to be heated 61, for example, the limb of a surgical or therapy patient, around which is wrapped a heat-conductive package 62, in this embodiment a sleeve 62 having sides 63, 64 and having a closed end 69 and an open end 68. Shown disposed within sleeve 62 is a heat pack 65 according to this invention. VELCRO® strips 70. 71 are used to secure the sleeve. Heat pack 65 may reside totally within sleeve 62, such that its third zone 66 is thermally coupled to the product 61. Alternatively, as shown by dashed lines, third zone 67 may lie outside sleeve 62 and be thermally isolated from the product 61, analogously to third zone 516 shown in FIG. 5.

Heat packs can be adapted for use in therapeutic applications. Certain injuries can be treated by the application of heat. These include muscle and ligament strains and sprains, as well as such afflictions as rheumatism and arthritis. Such applications might require that a heat pack be fashioned as a sleeve or a pad, and include fastening means, for example strips 126, 127 (FIG. 1) as described above.

Heat packs can also find use in remote wilderness areas for recreational purposes, or in rescue operations in any area where compact, self-heating devices are desired. For example, heat packs can be used to warm shock victims, or to treat or prevent frostbite. Heat packs also can be designed to heat food or for example, footwear. In such applications, a heat pack can be designed to assume an appropriate shape for its use.

The invention also features a method of heating a product with a self-heating, disposable heat pack. The method includes providing a heat pack, such as described above, in thermal contact with the product to be heated and compromising the first frangible separator. In some embodiments, a heat pack can be provided integrally with a container for a substance to be heated, such as a container for food or a drink. In other embodiments, a heat pack can be added to an object to be heated, or adapted to fit onto an object to be heated.

A number of embodiments of the invention have been described. Nevertheless, it will be understood that various modifications may be made without departing from the spirit and scope of the invention. For example, other chemicals may be used to initiate and support an exothermic chemical reaction, other container materials may be used, other heat sink materials may be used, and other applications for heat packs may be recognized. Accordingly, other embodiments are within the scope of the following claims.

What is claimed is:

1. A flexible disposable heating device conformable to a shape defined by its surroundings comprising a container having:

a first zone containing a fuel;

a second zone containing an oxidizer;

a collapsed third zone capable of serving as an expansion chamber;

a first frangible separator disposed between the first zone and the second zone, the first frangible separator being manually operable to provide communication therebetween, defining a reaction chamber comprising at least one of said first and second chambers;

a second frangible separator responsive to an exothermic chemical reaction within the reaction chamber, the second frangible separator being operable to provide vapor communication between the reaction chamber and the third zone;

wherein communication between the first zone and the second zone allows mixing of the fuel and the oxidizing agent to initiate an exothermic chemical reaction capable of generating a vapor; and wherein an environmental parameter associated with the exothermic chemical reaction operates the second frangible separator, permitting said vapor to flow into said third zone, thereby reducing pressure in the reaction chamber.

2. The disposable heating device of claim 1 wherein the environmental parameter associated with the exothermic chemical reaction comprises an elevated temperature.

3. The disposable heating device of claim 1 wherein the environmental parameter associated with the exothermic chemical reaction comprises an elevated pressure.

4. The disposable heating device of claim 1 further comprising a phase-change material thermally coupled to the third zone.

5. The disposable heating device of claim 1 further comprising a non-fuel gelling agent solution in at least one of said first zone, and said second zone, wherein communication between the gelling agent and the reaction chamber initiates gelation of the gelling agent to produce a non-fuel gel that moderates the rate of the reaction independently of dissolution of the gelling agent; and wherein a sufficient amount of the gelling agent exists to produce gel rapidly enough to prevent a temperature associated with the exothermic chemical reaction from exceeding a predetermined maximum value.

6. The disposable heating device of claim 1 further comprising:

a preformed stiffenable gel and a vaporizable solvent in the first zone;

wherein the oxidizing agent is embedded and dispersed throughout the second zone in a dissolvable binding agent;

wherein the dissolvable binding agent dissolves during the exothermic chemical reaction to controllably expose the oxidizing agent at a predetermined rate;

wherein the vaporizable solvent vaporizes when a temperature associated with the exothermic chemical reaction reaches a predetermined maximum value, thereby causing stiffening of the gel; and wherein a sufficient amount of preformed stiffenable gel exists to prevent the temperature associated with the exothermic chemical reaction from exceeding the predetermined maximum value.

7. The disposable heating device of claim 1 further comprising a plurality of at least one of the first zone and the second zone.

8. The disposable heating device of claim 1 wherein the vapor is steam.

9. The disposable heating device of claim 1 wherein the container is conformable to a shape defined by its surroundings.

10. The disposable heating device of claim 1 wherein the oxidizing agent is potassium permanganate.

11. The disposable heating device of claim 1 wherein the fuel is an oxidizable organic compound.

12. The disposable heating device of claim 1 further comprising a valve coupled to the container and operable to provide communication between either the first zone, the second zone, or the third zone and atmosphere, said valve being responsive to at least one of either temperature or pressure.

13. The disposable heating device of claim 1 further comprising a plurality of containers, each container being isolated from an adjacent container by a separator disposed there between.

14. The disposable heating device of claim 1 wherein the second frangible separator comprises frangible portions and sealed portions aligned in an alternating pattern.

15. The disposable heating device of claim 14 wherein each container comprises an independently operable first frangible separator.

16. The disposable heating device of claim 1 wherein the first zone and the second zone are in thermal contact with a product to be heated.

17. The disposable heating device of claim 16 wherein the product to be heated is food.

18. The disposable heating device of claim 16 wherein the product to be heated is a drink.

19. The disposable heating device of claim 16 wherein the product to be heated is a body part of a surgical patient.

20. The disposable heating device of claim 16 wherein the product to be heated is a body part of a patient undergoing therapy.

21. The disposable heating device according to claim 1, wherein said container comprises
    a flexible polymeric upper sheet and
    a flexible polymeric lower sheets.

22. The disposable heating device of claim 21 further comprising:
    a preformed stiffenable gel and a vaporizable solvent in the first zone;
        wherein the vaporizable solvent vaporizes when a temperature associated with the exothermic chemical reaction reaches a predetermined maximum value, thereby causing stiffening of the gel to moderate the exothermic chemical reaction.

23. The disposable heating device of claim 21 wherein the second frangible separator comprises a plurality of frangible portions and a plurality of non-frangible portions.

24. The disposable heating device of claim 23 wherein the frangible portions and non-frangible portions are linearly aligned in an alternating manner across the frangible separator.

25. The disposable heating device of claim 1 wherein compromise of the second frangible separator provides an increased internal volume that is approximately 101% to 200% greater than the initial internal volume of said first and second zones.

26. The disposable heating device of claim 21 wherein compromise of the second frangible separator provides an increased internal volume that is approximately 110% to 150% greater than the initial internal volume of said first and second zones.

27. A method of heating a product, the method comprising:
    providing a heating device according to claim 1 in thermal contact with the product, and
    compromising the first frangible separator to establish communication between the first zone and the second zone thereby initiating the exothermic chemical reaction and heating the product.

28. The method of claim 27 wherein the product to be heated comprises food.

29. The method of claim 27 wherein the product to be heated comprises a drink.

30. The method of claim 27 wherein the product to be heated comprises a body part of surgical patient.

31. The method of claim 27 wherein the heating device further comprises a plurality of containers, each container comprising a respective first frangible separator that is manually operable, the method further comprising compromising another first frangible separator to initiate a second exothermic chemical reaction.

32. A system for heating an object, comprising
    a thermally conductive package containing
    a heating device according to claim 1 disposed within the package.

33. The system of claim 32 wherein the package is a sleeve.

34. The system of claim 32 wherein the third zone is thermally coupled to a product to be heated.

35. The system of claim 32 wherein the third zone is thermally isolated from a product to be heated.

* * * * *